(12) United States Patent
Schlichte et al.

(10) Patent No.: US 9,305,390 B2
(45) Date of Patent: Apr. 5, 2016

(54) SYSTEM AND METHOD FOR MAPPING TWO-DIMENSIONAL IMAGE DATA TO A THREE-DIMENSIONAL FACETED MODEL

(75) Inventors: David R. Schlichte, Irving, TX (US); Robert M. Laramee, Fort Worth, TX (US); Robert A. Shepherd, Fort Worth, TX (US); Brian P. Corbett, Hewitt, TX (US)

(73) Assignee: Textron Innovations Inc., Providence, RI (US)

( * ) Notice: Subject to any disclaimer, the term of this patent is extended or adjusted under 35 U.S.C. 154(b) by 772 days.

(21) Appl. No.: 13/202,531

(22) PCT Filed: Feb. 23, 2010

(86) PCT No.: PCT/US2010/025057
§ 371 (c)(1),
(2), (4) Date: Aug. 19, 2011

(87) PCT Pub. No.: WO2010/099109
PCT Pub. Date: Sep. 2, 2010

(65) Prior Publication Data
US 2011/0298800 A1   Dec. 8, 2011

Related U.S. Application Data

(60) Provisional application No. 61/155,025, filed on Feb. 24, 2009.

(51) Int. Cl.
*G06T 15/04* (2011.01)
(52) U.S. Cl.
CPC ..................................... *G06T 15/04* (2013.01)

(58) Field of Classification Search
CPC .......... G06T 15/00; G06T 15/04; G06T 19/00
USPC .................................. 345/629, 419, 582, 420
See application file for complete search history.

(56) References Cited

U.S. PATENT DOCUMENTS

| | | | |
|---|---|---|---|
| 5,357,600 A * | 10/1994 | Shirman et al. | 345/520 |
| 5,461,712 A * | 10/1995 | Chelstowski et al. | 345/543 |
| 5,822,450 A | 10/1998 | Arakawa et al. | |
| 5,966,673 A * | 10/1999 | Shannon, Sr. | 702/35 |
| 7,259,760 B1 * | 8/2007 | Hashimoto et al. | 345/419 |
| 2001/0005204 A1 * | 6/2001 | Matsumoto et al. | 345/418 |

(Continued)

OTHER PUBLICATIONS

Williams et al, Perceptually Guided Simplification of Lit, Textured Meshes, 2003, Association for Computer Machinery, Inc., pp. 113-121 and p. 241.*

(Continued)

*Primary Examiner* — Haixia Du
(74) *Attorney, Agent, or Firm* — James E. Walton (57) ABSTRACT

A method for mapping a two-dimensional image data onto a three-dimensional graphic model of an object includes taking a plurality of two-dimensional images of the object. Each two-dimensional image has data, such as temperature data, which is desired to be represented on the three-dimensional graphic model. The three-dimensional model of the object is viewed on a graphic user interface. The three-dimensional model has a plurality of facets, each facet being configured for selectively receiving the data from the two-dimensional images, so that the two-dimensional images are mapped onto the facets of the three-dimensional model. The three-dimensional model can then be analyzed.

20 Claims, 8 Drawing Sheets

(56) References Cited

U.S. PATENT DOCUMENTS

| | | | |
|---|---|---|---|
| 2002/0060679 A1* | 5/2002 | Malzbender et al. | 345/423 |
| 2002/0154132 A1* | 10/2002 | Dumesny et al. | 345/582 |
| 2006/0087505 A1 | 4/2006 | Dumesny et al. | |
| 2006/0190178 A1 | 8/2006 | Zumora et al. | |
| 2006/0232583 A1 | 10/2006 | Petrov et al. | |
| 2007/0217672 A1 | 9/2007 | Shannon et al. | |
| 2007/0262983 A1 | 11/2007 | Choi | |
| 2009/0021522 A1* | 1/2009 | Burley et al. | 345/582 |
| 2009/0153577 A1* | 6/2009 | Ghyme et al. | 345/582 |
| 2013/0120375 A1* | 5/2013 | Jin et al. | 345/420 |

OTHER PUBLICATIONS

Shirmun et al, The Cone of Normals Technique for Fast Processing of Curved Patches, 1993, Eurographics '93, vol. 12, (1993) No. 3, pp. C-261-C-272.*

Sander et al, Silhouette Clipping, 2000, ACM SIGGRAPH 2000, pp. 1-8.*

Zockler et al, Interactive Visualization of 3D-Vector Fields Using Illuminated Stream Lines, 1996, 7$^{th}$ IEEE Visulization Conference (VIS '96), pp. 1-7.*

Luebke et al, Perceptually Guided Simplification of Lit, Textured Meshes, Apr. 2003, 2003 ACM SIGGRAPH Symposium on Interactive 3D Graphics, pp. 1-12.*

Hanrahan et al, Direct WYSIWYG Painting and Texturing on 3D Shapes, Aug. 1990, ACM, Computer Graphics, vol. 24, No. 4, pp. 215-223.*

NASA, Infrared Dog, Oct. 5, 2003, http://coolcosmos.ipac.caltech.edu/image_galleries/ir_zoo/dog.html, pp. 1.*

Office Action issued by the European Patent Office in corresponding application 10746706.0-1502 dated Sep. 24, 2013.

Genc S et al: "Texture extraction from photographs and rendering with dynamic texture mapping" Sep. 27, 1992 from Image Analysis and Processing, 1999. Proceedings, International Conference on Venice, Italy Sep. 27-29, 1999, Los Alamitos, CA USA, IEEE.

Hoegner Ludwig et al, "Texture extraction for building models from IR sequences of urban areas" 2007 Urban Remote Sensing Joint Event IEEE Piscataway, NJ USA Published Apr. 11, 2007 in Paris, France.

Janko Zsolt et al., Creating entirely textured 3D models of real objects using surface flattening from Machine Graphics & Vision Inst. Comput. Sci. Poland. vol. 14, No. 4, pp. 379-398.

Extended European Search Report issued by the European Patent Office in corresponding application 10746706.0-1502 dated Feb. 12, 2013.

Office Action from the corresponding Canadian Application No. 2,751,853 issued by the Canadian Intellectual Property Office dated Oct. 25, 2013, 3 pages.

International Search Report mailed by ISA/USA, U.S. Patent and Trademark Office on Apr. 12, 2010 for International Patent Application No. PCT/US10/25057.

International Preliminary Examination Report mailed by IPEA/US, U.S. Patent and Trademark Office on Feb. 22, 2011 for International Patent Application No. PCT/US10/25057.

Davis, Steven B., Real Time Application of Advanced Three-Dimensional Graphic Techniques for Research Aircraft Simulation. NASA Tech. Memo 101730. Dec. 1990, p. 8.

Summons to Attend Oral Proceedings dated Apr. 12, 2014 from counterpart EP App. No. 10746706.0.

Boyle E: "Creation and animation of virtual humans", Ambient Multimedia: Proceedings of 11 th International Workshop on Systems, Signals and Image Processing, Sep. 13-15, 2004, Poznan, Poland, Poznan University of Technology, Institute of Electronics and Telecommunications, Poland, pp. 143-146, XP008159726, dated Jan. 1, 2004 from counterpart EP App. No. 10746706.

Matsuyama T et al: "Real-Time Dynamic 3-D Object Shape Reconstruction and High-Fidelity Texture Mapping for 3-D Video", IEEE Transactions on Circuits and Systems for Video Technology, IEEE Service Center, Piscataway, NJ, US, vol. 14, No. 3, pp. 357-369, XP0111 08801, ISSN: 1051-8215,001: 10.11 09/TCSVT.2004.823396 dated Mar. 1, 2004 from counterpart EP App. No. 10746706.0.

Orzan A et al: "Omnidirectional texturing of human actors from multiple view video sequences", Proceedings of ACM SIGCHI Romanian Conference on EPO Form Computer-Human Interaction, pp. 133-136, XP55144237, Cluj-Napoca dated Jan. 1, 2005 from counterpart EP App. No. 10746706.0.

Rizzi A et al: "Digital Preservation, Documentation, and Analysis of Paintings, Monuments, and Large Cultural Heritage with Infrared Technology, Digital Cameras, and Range Sensors", Proc. of XXI Int. CIPA Symposium, pp. 1-6, XP055145382, Athens, Greece Retrieved from the Internet: URL:http://www.isprs.org/proceedings/xxxvi/5-c53/papers/fp125.pdf [retrieved on Oct. 9, 2014] dated Oct. 1, 2007 from counterpart EP App. No. 10746706.0.

Mahulikar et al: "Infrared signature studies of aerospace vehicles", Progress in Aerospace Sciences, Oxford, GB, vol. 43, No. 7-8,pp. 218-245, XP022357024, ISSN: 0376-0421, 001: 10.1 016/J.Paerosci.2007.06.002 dated Oct. 1, 2007 from counterpart EP App. No. 10746706.0.

* cited by examiner

SYSTEM AND METHOD FOR MAPPING TWO-DIMENSIONAL IMAGE DATA TO A THREE-DIMENSIONAL FACETED MODEL

TECHNICAL FIELD

The present application relates to systems and methods for mapping a two-dimensional image onto a three-dimensional graphical model.

DESCRIPTION OF THE PRIOR ART

It is often desirable to map two-dimensional image data onto a three-dimensional graphic model of an object. For example, when evaluating the survivability of an aircraft, it is desirable to map operating temperatures onto a computer-generated three-dimensional model of the aircraft. The temperature data may be provided in the form of multiple two-dimensional infrared radiation (IR) images taken of the aircraft taken from different angles while the aircraft is in operation. Past systems and methods of applying the temperature data onto the three-dimensional graphical model of the aircraft suffer from a number of shortcomings, as they tend to be very time consuming, tedious, and/or inaccurate.

One prior method is to simply transfer the data manually, by hand. Temperature data from IR images are simply looked at and are assigned as closely as possible to the proper facets on a hard copy of the appropriate aircraft model. This method is extremely time consuming, and not very accurate.

Another prior method involves command line scripting. The computer-generated three-dimensional model is modified at the script level, and then superimposed on an image to match temperatures to the proper facets. This method is more accurate than transferring the data by hand, but is still very time consuming and quite tedious. Also, the three-dimensional model is never displayed with the results of a mapping event (i.e., to show how the temperatures look on the three-dimensional model).

One other prior method involves the use of image processing utilities. Using image processing software on a computer, portions of IR images are selected by the user so that data from a particular region can be collected. The areas that are selected correspond to surfaces in the three-dimensional graphical model. This method does not lend itself to high resolution since each aircraft subdivision must be processed individually. Dividing the model into a large number of subdivisions makes the method time consuming and tedious. Error is also introduced since the user must accurately draw the outline of each region without any guidance since the aircraft model is not incorporated into the image processing software utility.

Hence, there is a need for an improved system and method for transferring two-dimensional image data onto a three-dimensional computer-generated graphical model.

BRIEF DESCRIPTION OF THE DRAWINGS

The novel features believed characteristic of the application are set forth in the appended claims. However, the system itself, as well as a preferred mode of use, and further objectives and advantages thereof, will best be understood by reference to the following detailed description when read in conjunction with the accompanying drawings, wherein:

While the system of the present application is susceptible to various modifications and alternative forms, specific embodiments thereof have been shown by way of example in the drawings and are herein described in detail. It should be understood, however, that the description herein of specific embodiments is not intended to limit the application to the particular forms disclosed, but on the contrary, the intention is to cover all modifications, equivalents, and alternatives falling within the spirit and scope of the system of the present application as defined by the appended claims.

DESCRIPTION OF THE PREFERRED EMBODIMENT

Illustrative embodiments of system of the present application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

The disclosed system and method allows for any two-dimensional data to be mapped to an existing three-dimensional model. Examples of two-dimensional data includes data representative of digital images, such as those that can be rendered by a computer on a computer monitor or other such display device based on electronic data, for example where the data is stored as a graphical image file in any of a number of known file formats including bmp, jpg, gif, tiff, png, and the like. Two-dimensional data can also be contained in a text file having a two-dimensional array or matrix of data. Similarly, examples of three-dimensional models include three-dimensional computer graphical models, such as wireframe representations of three-dimensional objects generated by any of a number of known software packages.

Some embodiments of the present system and method can be used in the rotorcraft and fixed-wing aircraft industries. For example, embodiments of the present system and method can be used in connection with infrared (IR), near IR, visible, and ultraviolet (UV) modeling. Such aircraft modeling is useful for evaluating aircraft survivability. By mapping temperatures to a three-dimensional model of an aircraft, IR simulations can be conducted on the model for a variety of environments and threats in order to predict the survivability and mission effectiveness of the aircraft.

Some embodiments can be used in other industries that utilize three-dimensional predictive modeling. For example, some embodiments can be applied in industries where texture mapping is desirable, such as architecture, three-dimensional terrain mapping, and commercial three-dimensional graphics, e.g., television, movies, and video games.

The following detailed description describes embodiments of the present system and method that enable a fast and accurate means for mapping temperatures from a two-dimensional IR image of an aircraft to a three-dimensional model of the aircraft using an intuitive graphical user interface (GUI). It will be appreciated that alternative embodiments can allow for mapping other image data from a two-dimensional image to a three-dimensional model of an object.

Figure 1:
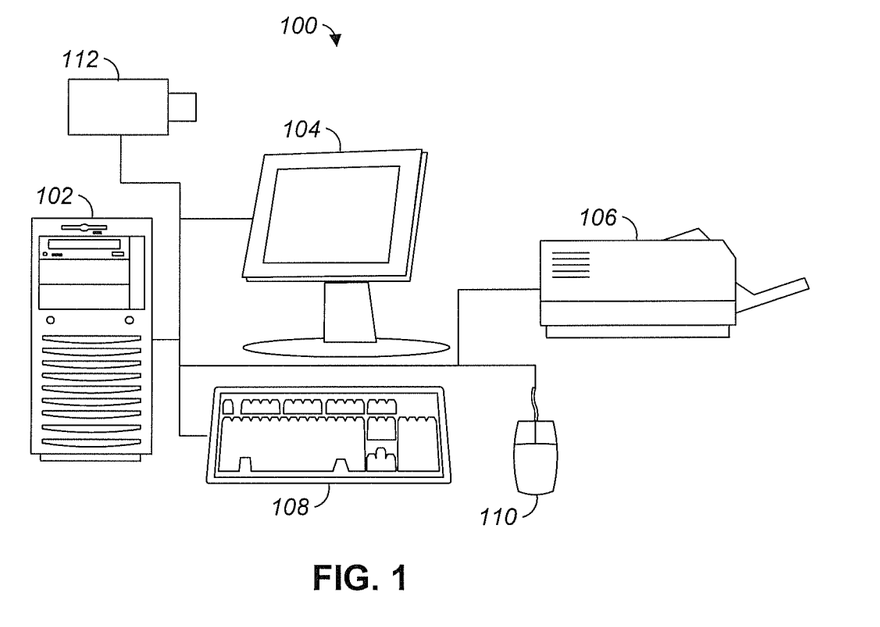
FIG. 1 shows a block diagram of an example of a specific machine that can serve as an embodiment of a system for mapping two-dimensional image data to a three-dimensional model.

Referring to FIG. 1 in the drawings, a block diagram is shown of an example of a specific machine that can serve as an embodiment of a system 100 for mapping two-dimensional image data to a three-dimensional model. System 100 includes a computer 102, which serves as a data storage system and a data processing system. Computer 102 includes components commonly associated with personal computers, workstations, and servers, such as a central processing unit (CPU), non-volatile memory, such as a hard drive, volatile memory, such as random access memory (RAM), communication ports and controllers, such as universal serial bus (USB) ports, and can also include networking and wireless communications subsystems for communicating with other computers and peripheral components. Computer 102 can also include means for communicating with removable storage media, such as a compact disc (CD), digital video disc (DVD), and solid state memory such as a flash memory USB drive. System 100 also includes a display 104 and a printer 106, which both serve as examples of output devices for computer 102. Printer 106 can be a two-dimensional printer, such as a plotter, laser printer, or ink jet printer. The system 100 further includes a keyboard 108, a mouse 110, and a camera 112, which all serve as examples of input devices for the computer 102. Camera 112 can be any conventional digital camera, including IR cameras capable of taking still pictures in the IR range. For example, camera 112 can be a thermographic IR camera.

Computer 102 can perform operations for mapping two-dimensional image data to a three-dimensional model as described herein. Computer 102 can perform such operations according to software instructions stored at computer 102, for example on a hard drive or on a CD or DVD, or stored remotely on another computer or server. Where instructions are stored remotely, some or all of the computer processing may be performed by computer 102 and/or by the remote computer or server.

Figure 2:
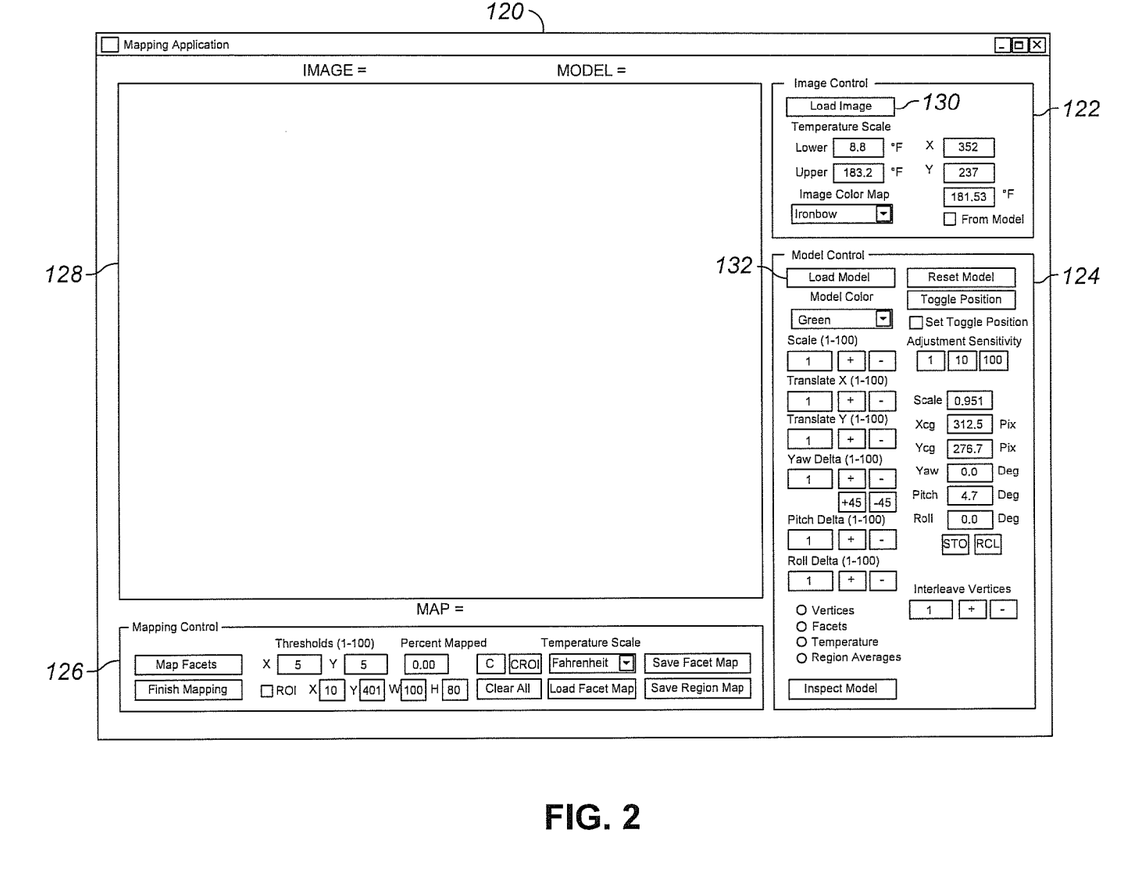
FIGS. 2-5 show a graphical user interface for the system shown in FIG. 1.

Referring next to FIG. 2, computer 102 generates a GUI, such as the illustrated GUI 120. Computer 102 controls display 104 to display the GUI 120. GUI 120 includes image control section 122, model control section 124, mapping control section 126, and an image window 128. A user can interact with GUI 120 using an input device, for example keyboard 108 and/or mouse 110.

Image control section 122 includes "Load Image" button 130 that the user can activate in order to select and load an image into image window 128. Similarly, model control section 124 includes a "Load Model" button 132 that the user can activate in order to select and load a three dimensional model into image window 128. The "Load Image" button 130 can be activated by the user for initiating a subroutine for allowing the user to select an electronic image file, for example which may be stored locally or remotely, for example on computer 102, on camera 112, or on a remote server (not shown). The user can select the desired image file, and in response the selected image file is loaded and displayed (e.g., as image 134 shown in FIG. 3) in image window 128. Similarly, the "Load Model" button 132 can be activated by the user for allowing the user to select and load an electronic model file stored locally or remotely.

Figure 3:
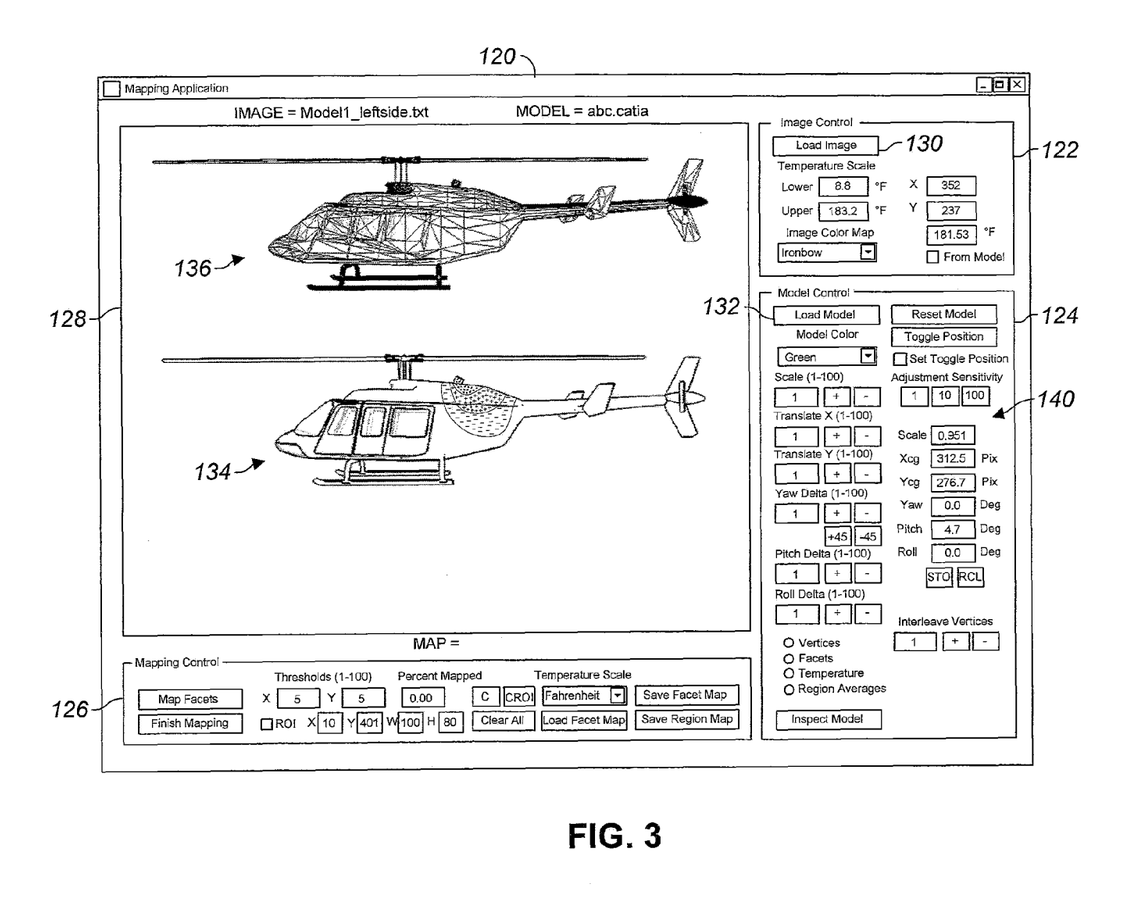

Referring next to FIG. 3, the GUI 120 is shown after a user has loaded an image 134 of a rotorcraft and a three-dimensional model 136 of the same or similar rotorcraft. The image control section 122 and model control section 124 include graphic positioning tools for allowing the user to align model 136 with image 134. In some embodiments, the user can move image 134, for example by clicking and dragging image 134 using the mouse 110. The model 136 can be translated, scaled, and rotated using the Scale, Translate X, Translate Y, Yaw Delta, Pitch Delta, and Roll Delta controls 140, which also include text fields containing current text values that can also be used for adjusting the position, orientation, and size of model 136. It should also be appreciated that the alignment of image 134 and model 136 can be implemented using software which automatically aligns image 134 and model 136. Note that in FIG. 3, three-dimensional model 136 has been rotated and scaled to match the orientation of the rotorcraft in image 134.

The three-dimensional model 136 is a wireframe model of the rotorcraft. The wireframe model includes a number of faceted surfaces that approximate the respective regions of the actual aircraft surfaces. The wireframe model is made up of X, Y, and Z coordinate node points connected by straight lines to form triangular or quadrilateral facets. The connected facets form a 3-dimensional surface geometry representation of a target object or surface. The three-dimensional model 136 can be created according to any of a number of known processes for created three-dimensional models of an object.

Image 134 is a two-dimensional representation of the aircraft. Image 134 can be a digital image that was taken by camera 112. In the illustrated embodiment, the drawing of image 134 represents a thermal image of an aircraft. Actual implementations can utilize conventional thermal images that vary in color depending on the intensity of the infrared emission, which varies according to the temperature of the photographed objects. For example, in some thermal images, a hotter region will appear brighter than a cooler region. Alternatively, regular photographic still images can be used, for example for applying a texture to a three-dimensional wireframe model.

Figure 4:
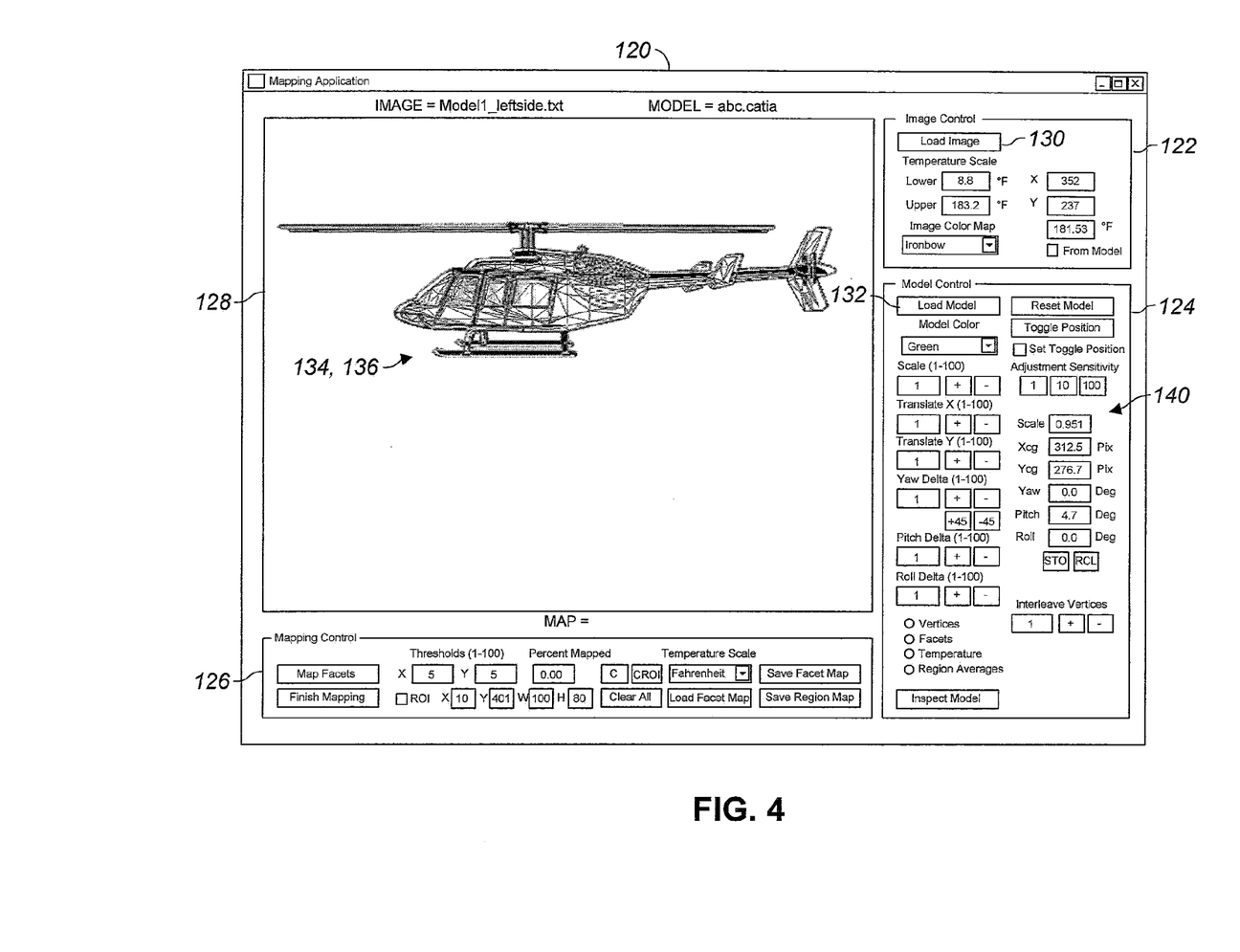

Referring next to FIG. 4, GUI 120 is shown after the user has aligned the image 134 with the three-dimensional model 136. The user can now use the mapping control section 126 for mapping the thermal image information from image 134 onto three-dimensional model 136. The mapping control section 126 provides user controls for setting facet acceptance parameters or thresholds, which are used for masking facets of the model 136 from being mapped using the current image 134.

Figure 5:
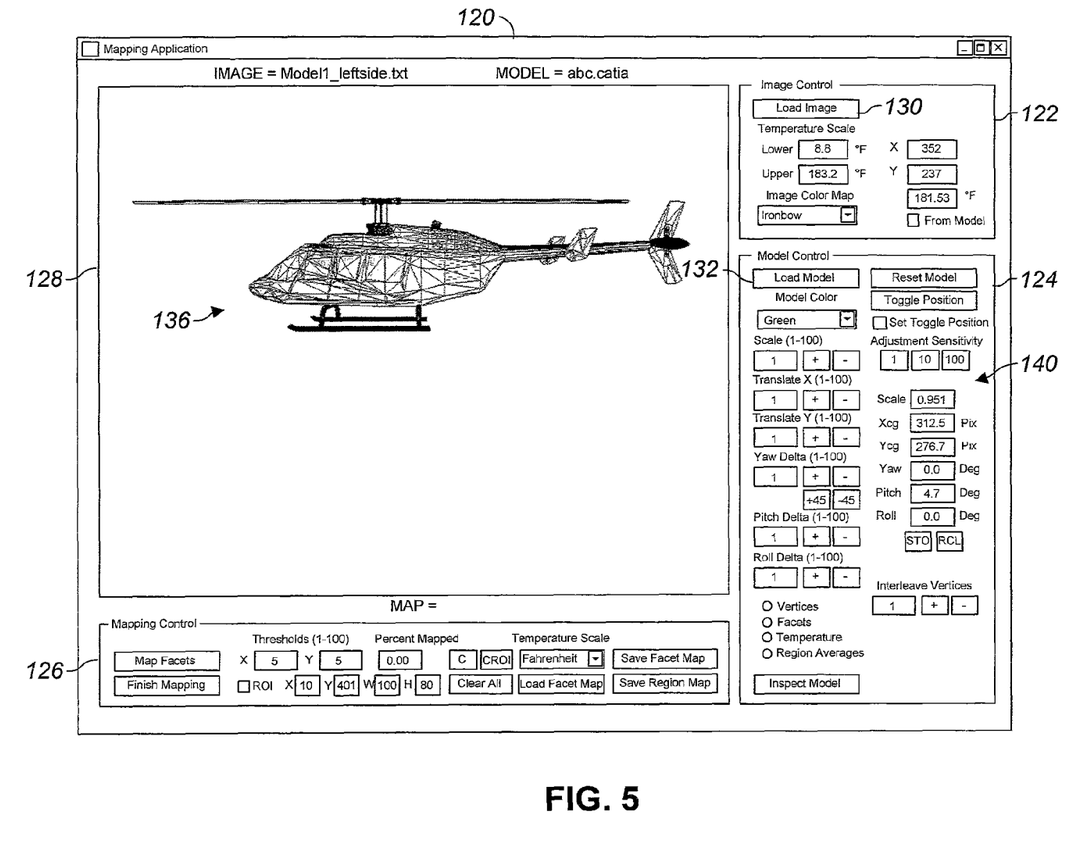

FIG. 5 shows the results of the mapping process, where the thermal image information has now been applied to certain facets of model 136. The mapping and masking process will be described in greater detail below in connection with FIGS. 6A-6C, 7, and 8.

Figure 6A:
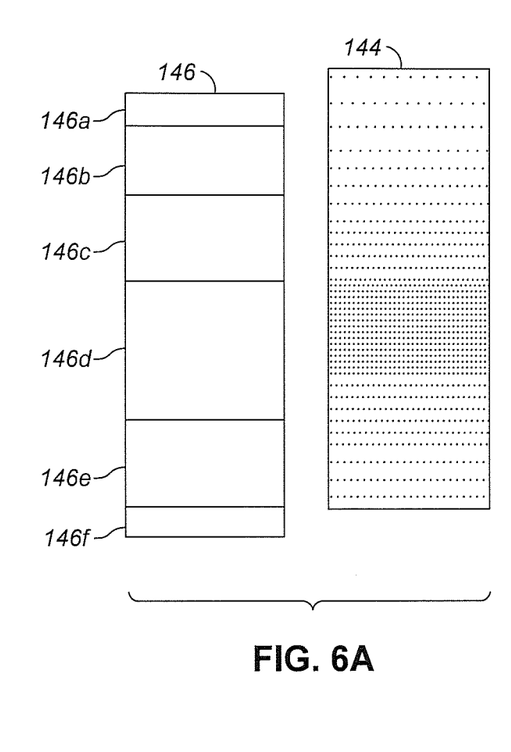
FIGS. 6A-6C show diagrams of various steps in a mapping process used by the system shown in FIG. 1.
Figure 6B:
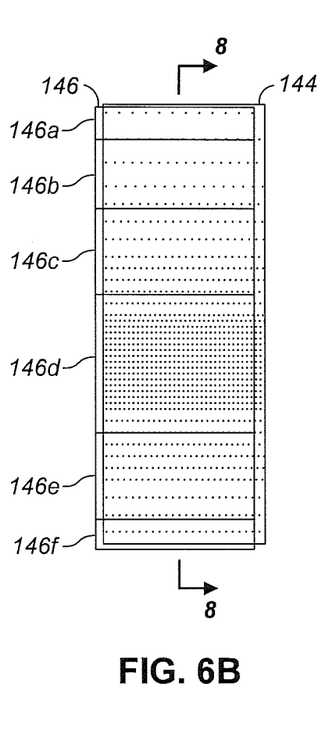
Figure 6C:
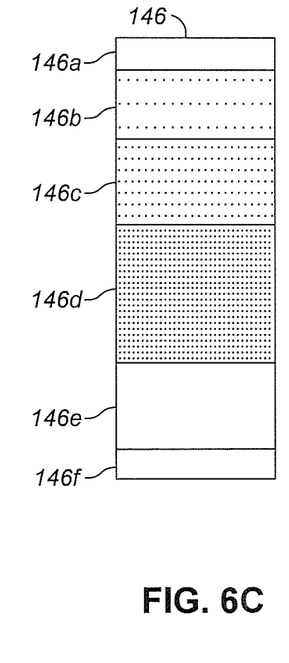

Turning next to FIGS. 6A-6C, the process shown in FIGS. 3-5 is described in greater detail with reference to FIGS. 6A-6C, as well as FIGS. 7 and 8.

Referring first to FIG. 6A, an image or portion of an image generally designated as image 144 can be, for example, a portion of an image, such as image 134, that has been loaded into the image window 128 of the GUI 120. A portion of a three-dimensional model generally designated as model 146 can be, for example, a portion of a three-dimensional model, such as model 136, that has also been loaded into the image window 128 of the GUI 120. Model 146 includes a plurality of facets 146a-146f. Image 144 includes surface indicia that can be ornamental or representative of some information, such as temperatures. The view shown in FIG. 6A corresponds with the situation shown in FIG. 3, where an image 134 and a model 136 have been loaded into the image window 128 of the GUI 120.

Referring next to FIG. 6B, image 144 and model 146 have now been substantially aligned such that regions of image 144 are at least somewhat aligned with corresponding regions of the model 146. This corresponds to the situation shown in FIG. 4. Image 144 and model 146 can be aligned using the positioning controls 140 in the GUI 120. Once image 144 and model 146 are aligned as desired by the user, or an automated process, the surface indicia of image 144 can be mapped to model 146.

Referring next to FIG. 6C, the result of the mapping process is shown. Portions of the surface indicia from image 144 have been applied to respective closest facets 146b-146d of model 146. However, it will be noted that no surface indicia has been applied to facets 146a, 146e, and 146f. Facets 146a, 146e, and 146f were masked during the mapping process in order to prevent the application of the surface indicia from image 144 from being applied thereto.

Figure 8:
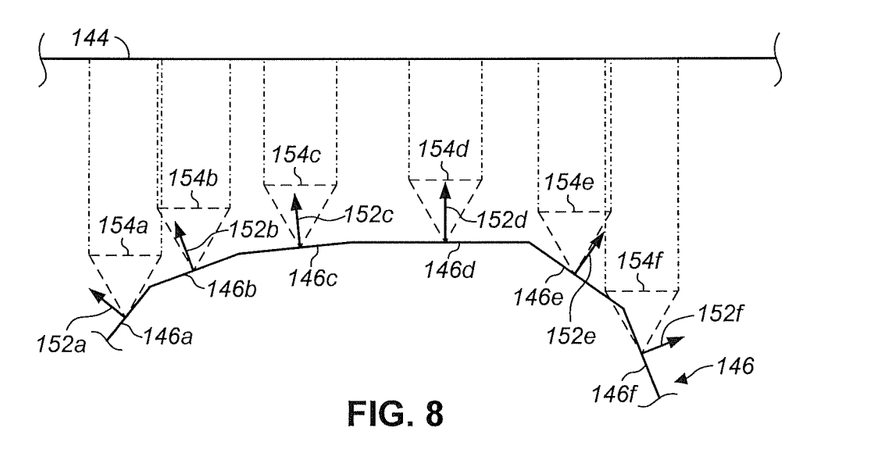

Turning momentarily to FIG. 8, the reason for masking certain facets 146a-146f can be better understood with reference to FIG. 8, which shows a virtual cross-sectional view of taken along section lines 8-8 in FIG. 6B. Model 146 represents a three dimensional object composed of facets 146a-146f that are at various different angles relative to the plane of image 144. In some cases, the angle between any facet 146a-146f and image 144 can be so great that it may be considered undesirable to apply the surface indicia of image 144 to the corresponding facet 146a-146f. For example, the user may have another image showing a better view of any facet 146a-146f, and therefore may desire to use the surface indicia from the other image. So, in the present example, facets 146a, 146e, and 146f are at angles that are considered by the user to be too great for mapping from the current image 144. Thus, based on inputs from the user, the facets 146a, 146e, and 146f are detected to be facets that should be masked.

The masking process will be now described in greater detail with reference to FIGS. 7 and 8.

Figure 7:
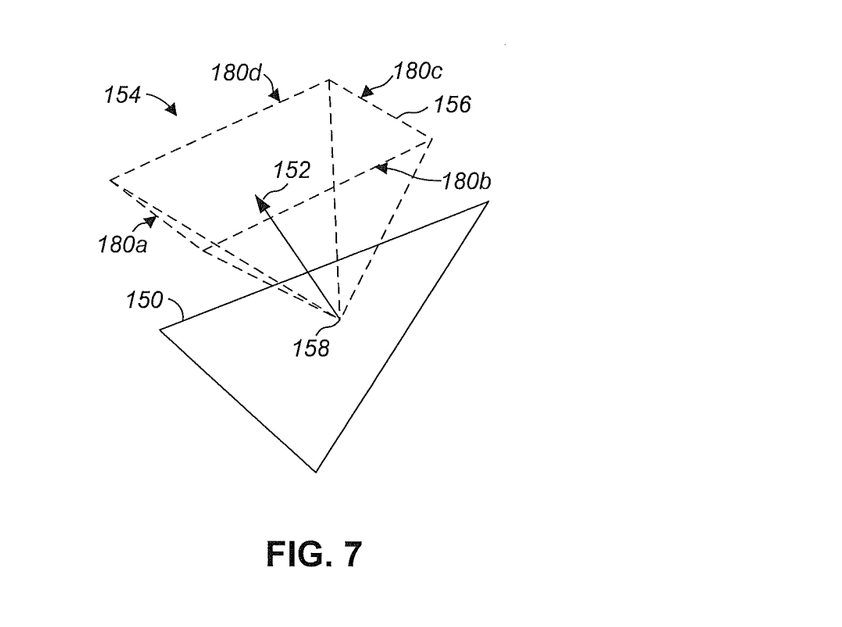
FIGS. 7 and 8 show diagrams for explaining a masking process that can be included in the mapping process.

Referring next to FIG. 7, as discussed above, each three-dimensional model is composed of a number of facets. For example, model 136 is composed of a number of facets, such as facet 150 shown in FIG. 7, and model 146 is composed of a number of facets 146a-146f shown in FIGS. 6A-6C and FIG. 8. While facet 150 is triangular and facets 146a-146f are rectangular, other shapes can be used. Facet 150 has a normal vector 152, which is normal to the plane of facet 150. Normal vector 152 can be obtained from the model data, which typically includes information about facet orientation and/or region definition. Facet 150 also has a virtual unit cone 154 (also referred to as an acceptance cone 154) generated by system 100 and shown in broken lines in FIG. 7. Base 156 of acceptance cone 154 is rectangular and defines a plane that is coplanar to the display surface, e.g., the viewing surface of display 104, and also coplanar to the image plane, e.g., the plane defined by image 134. In the example shown in FIG. 8, base 156 of acceptance cone 154 would be coplanar to the image plane of image 144. A vertex 158 of acceptance cone 154 coincides with the base of normal vector 152.

Since base 156 of acceptance cone 154 is rectangular, acceptance cone 154 includes four sides 180a-d that each extend between respective edges of the base 156 and vertex 158. Sides 180a-180d of the acceptance cone 154 define acceptance boundaries for facet 150. The angle between sides 180a-180d of acceptance cone 154 and base 156 of acceptance cone 154 is fixed by the system 100 and can be based on a predetermined default value or based on inputs from the user, via thresholds 178 (shown in FIG. 9), regarding an angle to be used as a threshold for masking purposes. If the normal vector 152 is inside the acceptance cone 154, then facet 150 is considered to be close enough to being coplanar with the image, e.g., image 134, for mapping. If normal vector 152 is outside of the acceptance cone 154, then facet 150 is masked and will not be mapped with data from the image. Thus, the internal volume of acceptance cone 154 defines an acceptance volume within which normal vector 152 must reside if facet 150 is to be mapped. Otherwise, the facet 150 will be treated as a masked facet and will not be mapped.

Referring again to FIG. 8, system 100 has generated acceptance cones 154a-154f for each of the respective facets 146a-146f. Each of the facets 146a-146f has a respective normal unit vector 152a-152f, such that each of the unit vectors 152a-152f is normal to its respective one of the facets 146a-146f. The base of each of the acceptance cones 154a-154f is coplanar to image 144, and the vertex of each of the acceptance cones 154a-154f is positioned at the base of respective unit vectors 152a-152f of respective facets 146a-146f. The sides of all of the acceptance cones 154a-154f are at a same predetermined angle relative to the base of the cones and, therefore, also to the plane of image 144. As shown in FIG. 8, the unit vectors 152a, 152e, and 152f all extend outside of the respective acceptance cones 154a, 154e, and 154f. Therefore, as shown in FIG. 6C, the corresponding facets 146a, 146e, and 146f are masked, meaning that facets 146a, 146e, and 146f will not be mapped to receive the surface indicia from image 144. The remaining facets 146b-146d all have respective unit vectors 152b-152d that are within respective acceptance cones 154b-154d. Therefore, facets 146b-146d are mapped to image 144 and receive the surface indicia from image 144 as shown in FIG. 6C.

Figure 9:
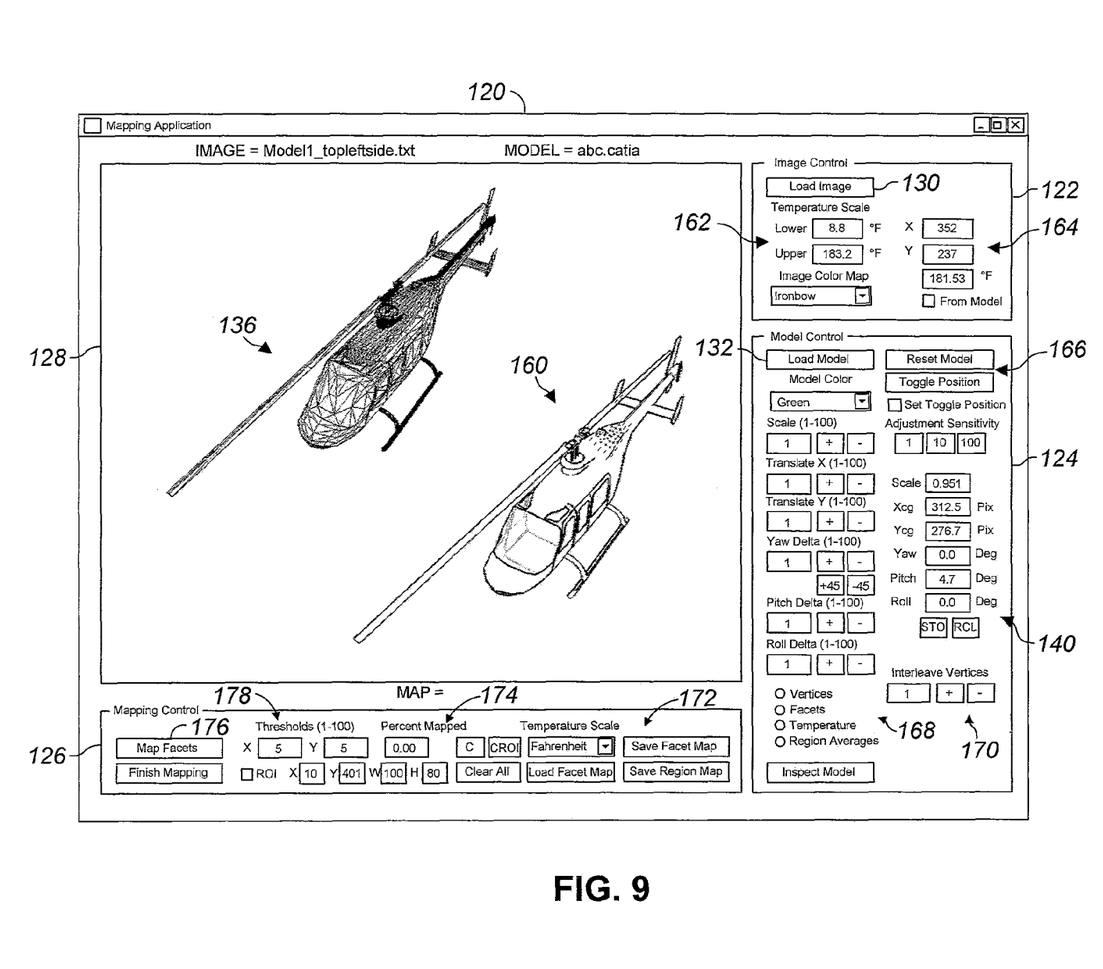
FIG. 9 shows another view of the graphical user interface for the system shown in FIG. 1.

Turning next to FIG. 9, the process shown in FIGS. 3-5 can continue using a different image 160, which is an image of the aircraft taken from a different angle compared to that of image 134. The model 136 is rotated and scaled to match the orientation of the rotorcraft in image 160. The process can then continue as described above for mapping further facets of model 136 using image 160, and then using still further images of other sides of the aircraft as desired. Using multiple images, such as images 134 and 160, showing various sides of the aircraft, model 136 can be partially or fully covered with surface indicia from the images. In some embodiments, system 100 can be configured such that any facet that has been mapped using an earlier image will automatically be masked so that the mapped surface indicia are not overwritten by later images. Additionally, a filling feature may be used to fill any unfilled facet in model 136 by applying data of the nearest filled facet to the unfilled facet.

Images or other renderings of model 136 can then be output, for example to a display such as display 104 for study in a virtual environment. For example, system 100 can include an "inspect model" mode, which is a 3D rendering and inspection mode. System 100 can also generate various output files containing data that can be used for studying the object represented by model 136. For example, system 100 can output one or more text files that contain a log of the mapping for each facet. In some embodiments, groups of facets can be combined into regions; for example, 24,000 facets can be reduced to 300 regions. The regions can be defined during creation of model 136. So, for example, in embodiments where images 134 and 150 are thermographs and temperature information is mapped to model 136, region average temperatures can be calculated and incorporated back into the model data. Also, the data for the temperature region map can include information about the number of facets in each region, along with mean and standard deviation temperature data, which can be used to check the quality of the region definitions. Once the temperature information is mapped to model 136 from the thermograph images, an IR signature for the aircraft (or other object) can be determined, for example using known software such as SPIRITS which works with region temperature data. The technique for determining an IR signature can include performing a spectral analysis, which can be compiled and evaluated for survivability information.

Continuing now to refer to FIG. 9, it will be appreciated that GUI 120 can include some additional user controls that may not be necessary in all embodiments.

The image controls 122 can include temperature scale input fields 162, which can be used for adjusting the temperatures associated with colors in the thermograph. Also, coordinate fields 164 can be used to select a point on the thermograph (e.g., using X-Y coordinates in the image window 128) and see the temperature for the selected point.

The model controls 124 can include reset and toggle-position controls 166. These can be used to reset the position/orientation of model 136 to default and for toggling the position or visibility of the model 136. Model 136 can be displayed in any of a number of different ways using the "inspect model options 168. For example, model 136 can be viewed as a series of model vertices. Model controls 124 can also include "interleave vertices" controls 170, which can be used for adjusting, e.g., thinning, model 136 in vertices view.

The mapping controls can include temperature scale controls 172, which allows the user to select a temperature scale (e.g., Fahrenheit, Celsius, etc.). A "Percent Mapped" field 174 can be provided to display the current percentage of the model 136 that has been mapped. A "map facets" button 176 is provided for allowing the user to initiate the mapping process once the model 136 and image 134, 160 are aligned. Threshold controls 178 allow the user to make adjustments for the masking process, which control the size and aspect ratio of acceptance cone 154.

It is apparent that an application with significant advantages has been described and illustrated. Although the present application is shown in a limited number of forms, it is not limited to just these forms, but is amenable to various changes and modifications without departing from the spirit thereof.

The invention claimed is:

1. A method for mapping two-dimensional image data onto a three-dimensional graphic model of an object, comprising:
   obtaining a first two-dimensional image of the object, the first two-dimensional image having data pertaining to the object;
   viewing a three-dimensional model of the object on a graphic user interface, the three-dimensional model having at least a first facet and a second facet;
   aligning the first two-dimensional image with the three-dimensional model on the graphic user interface;
   generating an acceptance cone for each facet so as to provide a geometry which defines acceptable mapping criteria based upon a threshold angle from a user, each acceptance cone having a rectangular cone base which is coplanar with a display surface;
   generating a normal vector associated with the first facet;
   mapping the data from the first two-dimensional image onto at least the first facet in the three-dimensional model based upon the normal vector associated with the first facet being located inside the acceptance cone associated with the first facet; and
   masking the first facet so as to prevent data from the two-dimensional image from mapping onto the first facet based upon the normal vector associated with the first facet being located outside the acceptance cone associated with the first facet;
   wherein each acceptance cone also having a vertex which coincides with a vector base of the normal vector;
   wherein aligning the first two-dimensional image with the three-dimensional model occurs by at least one of the following methods;
   moving the first two-dimensional image;
   translating the three-dimensional model;
   scaling the three-dimensional model; and
   rotating the three-dimensional model.

2. The method according to claim 1, wherein the mapping the data from the first two-dimensional image onto at least the first facet in the three-dimensional model comprises:
   masking the second facet so as to prevent data from the two-dimensional image from mapping onto the second facet.

3. The method according to claim 2, wherein masking the second facet so as to prevent data from the first two-dimensional image from mapping onto the second facet is based upon a normal vector associated with the second facet being located outside the acceptance cone associated with the second facet.

4. The method according to claim 1, further comprising:
   obtaining a second two-dimensional image of the object, the second two-dimensional image having a data pertaining to the object from a different orientation as that of the first two-dimensional image;
   aligning the second two-dimensional image with the three-dimensional model on the graphic user interface; and
   mapping the data from the second two-dimensional image onto at least the second facet in the three-dimensional model.

5. The method according to claim 4, further comprising:
   preventing the data from the second two-dimensional image from remapping onto at least the first facet in the three-dimensional model;
   wherein preventing the data from the second two-dimensional image from remapping onto at least the first facet in the three-dimensional model is based upon a normal vector associated with the first facet being located inside the acceptance cone associated with the first facet.

6. The method according to claim 1, wherein at least one of the first facet and the second facet is triangular.

7. The method according to claim 1, wherein at least one of the first facet and the second facet is rectangular.

8. The method according to claim 1, wherein aligning the first two-dimensional image with the three-dimensional model on the graphic user interface is performed by the user.

9. The method according to claim 1, wherein aligning the first two-dimensional image with the three-dimensional model on the graphic user interface is performed by an automated process.

10. The method according to claim 1, wherein the data from the first two-dimensional image includes temperature data.

11. The method according to claim 1, wherein the three-dimensional model, after mapping the data from the first two-dimensional image onto at least the first facet in the three-dimensional model, is a model having information for developing an infrared radiation signature of the object.

12. The method according to claim 11, wherein the object is an aircraft.

13. The method according to claim 1, wherein the first two-dimensional image of the object is a thermographic image.

14. A method for mapping a two-dimensional image data onto a three-dimensional graphic model of an object, comprising:
   taking a plurality of two-dimensional images of the object, each two-dimensional image having data;
   viewing a three-dimensional model of the object on a graphic user interface, the three-dimensional model having a plurality of facets;
   mapping the data from the plurality of two-dimensional images onto the three-dimensional model;
   generating an acceptance cone associated with individual facets of the three-dimensional model, the acceptance cone being based upon a selective threshold angle and an aspect ratio from a user, each acceptance cone having a rectangular cone base sized relative to the aspect ratio which is coplanar with a display surface, each acceptance cone also having a vertex which coincides with a vector base of a normal vector; and
   analyzing the three-dimensional model, after the data from the plurality of two-dimensional images has been mapped onto the three-dimensional model, so as to develop a temperature analysis of the object;
   wherein a side of the acceptance cone is equal to the selective threshold angle;
   wherein the mapping the data from the plurality of two-dimensional images onto the three-dimensional model is based upon the vector associated with the facet being located inside the acceptance cone associated with the facet.

15. The method according to claim 14, wherein the object is an aircraft and the temperature analysis represents an infrared radiation signature.

16. The method according to claim 14, wherein the two-dimensional images include selected colors, the colors being associated with selected temperatures.

17. The method according to claim 14, wherein the mapping of the data from the plurality of two-dimensional images onto the three-dimensional model includes individually mapping the data from each of the two-dimensional images until the desired facets of the three-dimensional model have been mapped.

18. The method according to claim 14, wherein the plurality of facets are shapes in a three-dimensional environment, each facet being representative of a portion of an outside surface of the object.

19. The method according to claim 14, wherein the three-dimensional object is a wireframe model having a plurality of node points in a three-dimensional space, each node point being connected to at least another node point with a line, thereby forming a plurality of facets.

20. The method according to claim 14, further comprising:
   masking a specified facet to prevent mapping the data from the plurality of two-dimensional images onto the specified facet of the three-dimensional model;
   wherein the masking of the specified facet is due to a portion of the normal vector of the specified facet being located outside of the acceptance cone.

* * * * *